United States Patent [19]

Hartmann et al.

[11] Patent Number: 4,748,220

[45] Date of Patent: May 31, 1988

[54] PREPARATION OF FINELY DIVIDED PULVERULENT CROSSLINKED COPOLYMERS

[75] Inventors: Heinrich Hartmann, Limburgerhof; Walter Denzinger, Speyer, both of Fed. Rep. of Germany

[73] Assignee: BASF Aktiengesellschaft, Ludwigshafen, Fed. Rep. of Germany

[21] Appl. No.: 28,307

[22] Filed: Mar. 20, 1987

[51] Int. Cl.$^4$ ............................ C08F 2/00; C08F 26/00
[52] U.S. Cl. ...................................... 526/89; 526/219; 526/227; 526/312; 526/307.6; 526/278; 526/318.6; 526/307.8; 526/329.1
[58] Field of Search ............... 526/312, 89, 318.6, 526/307.8, 329.1, 278, 307.6, 219, 227

[56] References Cited

U.S. PATENT DOCUMENTS

| | | | |
|---|---|---|---|
| Re. 29,231 | 5/1977 | Leeds | 424/80 |
| 3,040,012 | 6/1962 | Maeder | 526/89 |
| 3,522,228 | 7/1970 | Fukui et al. | 526/89 |
| 4,052,343 | 10/1977 | Cunningham | 526/312 |
| 4,418,175 | 11/1983 | Probst et al. | 526/312 |
| 4,486,489 | 12/1984 | George | 526/312 |

FOREIGN PATENT DOCUMENTS 753433  9/1970  France .................. 526/312

*Primary Examiner*—Joseph L. Schofer
*Assistant Examiner*—N. Sarofim
*Attorney, Agent, or Firm*—Bill B. Panagos

[57] ABSTRACT

Pulverulent crosslinked copolymers are prepared by polymerizing monomer mixtures consisting of
(a) from 70 to 99.99% by weight of monoethylenically unsaturated carboxylic acids, their amides and/or esters of such carboxylic acids and aminoalcohols,
(b) from 0.001 to 10% by weight of a diethylenically or polyethylenically unsaturated monomer and
(c) from 0 to 20% by weight of other monoethylenically unsaturated monomers in supercritical carbon dioxide under superatmospheric pressure in the presence of a free radical initiator.

6 Claims, No Drawings

PREPARATION OF FINELY DIVIDED PULVERULENT CROSSLINKED COPOLYMERS

Pulverulent crosslinked copolymers can be prepared by copolymerizing monomers in the presence of a crosslinking agent by various methods, for example by precipitation polymerization in benzene or a chlorohydrocarbon according to U.S. Pat. No. 2,798,053 or by reverse suspension polymerization by the method described in U.S. Pat. No. 4,059,552. In every case, a diluent is required. In the preparation of thickeners based on crosslinked polyacrylic acids or polyacrylamides, benzene, toluene, xylene and halohydrocarbons have proven particularly useful as inert diluents. However, these diluents also have the disadvantage since the copolymers prepared therein still contain smaller or larger amounts of inert diluents, such as aromatic hydrocarbons or halohydrocarbons, even after drying. Since some of the stated hydrocarbons are regarded as physiologically unacceptable or impart an intense odor to the copolymers, they have to be substantially removed from the copolymers. This necessitates purification operations, which are involved and expensive and furthermore do not permit complete removal of the troublesome solvents.

U.S. Pat. No. 3,522,228 discloses a process for the preparation of polymers, in which ethylenically unsaturated monomers are subjected to homopolymerization or copolymerization in the presence of a catalyst in liquid carbon dioxide at from $-78°$ to $100°$ C. under superatmospheric pressure. The polymers are obtained in the form of coarse powders or viscous oils from which they are precipitated by treatment of the liquids in which the polymers are insoluble.

It is an object of the present invention to provide a process which gives pulverulent crosslinked copolymers by copolymerization of the monomers in a diluent which is physiologically acceptable and can be readily removed from the polymers.

We have found that this object is achieved, according to the invention, by a process for the preparation of pulverulent crosslinked copolymers by polymerization of a monomer mixture consisting of (a) from 70 to 99.999% by weight of monoethylenically unsaturated carboxylic acids, amides of such carboxylic acids and/or esters of such carboxylic acids and aminoalcohols of the formula

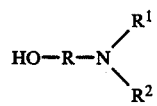

where R is $C_2$–$C_6$-alkylene and $R^1$ and $R^2$ are each H, $CH_3$, $C_2H_5$ or $C_3H_7$, (b) from 0.001 to 10% by weight of a diethylenically or polyethylenically unsaturated monomer and (c) from 0 to 20% by weight of other monoethylenically unsaturated monomers, in an inert diluent in the presence of a free radical initiator, and removal of the diluent, if the copolymerization is carried out under superatmospheric pressure in supercritical carbon dioxide as the inert diluent, with thorough mixing, at up to $150°$ C. and under a pressure above 73 bar, and from 100 to 1,500 parts by weight of carbon dioxide are used per 100 parts by weight of the monomers.

Suitable monomers of group (a) are primarily monoethylenically unsaturated carboxylic acids. The most important members of this group are, for example, monoethylenically unsaturated $C_3$–$C_5$-carboxylic acids, such as acrylic acid, methacrylic acid, vinylacetic acid, itaconic acid, crotonic acid, alpha-methylcrotonic acid, alpha-ethylacrylic acid, dimethylacrylic acid, alpha-chloroacrylic acid and vinyllactic acid. The amides of monoethylenically unsaturated carboxylic acids, eg. acrylamide, methacrylamide, crotonamide and itaconamide, are also suitable. The monomers of group (a) furthermore include esters of monoethylenically unsaturated carboxylic acids and aminoalcohols of the formula

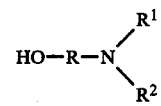

where R is $C_2$–$C_6$-alkylene and $R^1$ and $R^2$ are each H, $CH_3$, $C_2H_5$ or $C_3H_7$. These compounds are preferably di-$C_1$–$C_3$-alkylamino-$C_2$–$C_6$-alkyl acrylates or methacrylates. Specific examples of these monomers are diacrylates. methylaminoethyl acrylate, dimethylaminoethyl methacrylate, diethylaminoethyl methacrylate, diethylaminoethyl acrylate, dipropylaminoethyl acrylate, dimethylaminopropyl acrylate, dimethylaminopropyl methacrylate, dimethylaminobutyl acrylate, dimethylaminobutyl methacrylate, dimethylaminobutyl methacrylate, dimethylaminoneopentyl acrylate, dimethylaminoneopentyl methacrylate and dimethylaminohexyl acrylate. The stated basic acrylates and methacrylates are preferably used in the form of the salts with mineral acids or carboxylic acids (eg. hydrochloric acid, sulfuric acid, formic acid, acetic acid or propionic acid) or in quaternized form. Examples of suitable quaternizing agents are dimethyl sulfate, methyl chloride, ethyl chloride, lauryl chloride and benzyl chloride.

The monomers of group (a) can be subjected, either alone or as a mixture, to the copolymerization with the monomers (b). Of the monomers of group (a), acrylic acid, methacrylic acid, acrylamide and/or methacrylamide are preferably used. If acrylic acid is used as monomer (a), a crosslinked polyacrylic acid is obtained by copolymerization with the monomers of group (b); similarly, the use of acrylamide as the monomer of group (a) gives crosslinked polyacrylamides. If mixtures of acrylic acid and acrylamide are used as the monomers of group (a), crosslinked copolymers of acrylamide and acrylic acid are obtained in the copolymerization. Another variant of crosslinked copolymers is obtained if either acrylic acid or acrylamide is copolymerized with the monomers (b) and, where relevant, the monomers of group (c) also in the presence of dimethylaminoethyl acrylate. Since the monomers of group (a) can be copolymerized with one another in any ratio, there is a wide range of possible compositions of the crosslinked copolymers. The copolymers are composed of from 70 to 99.95% by weight of the monomers of group (a).

Monomers containing two or more ethylenically unsaturated double bonds, eg. divinylbenzene, divinyl ketone, butanediol diacrylate, ethylene glycol diacrylate, butanediol dimethacrylate, ethylene glycol dimethacrylate, methylenebisacrylamide, diallyl phthalate, divinyl ether, divinyldioxane, polyalkenyl polyethers, such as polyallyl and polyvinyl ethers of mono-, di- and oligosaccharides, eg. tri-, tetra-, penta- and hexaallyl sucrose and mixtures of these, pentaerythritol triallyl ether, di- and triallyl ethers of trimethylolpropane and diallylacrylamide, polyallyl- and polyvinylsilanes, triallyl cyanurate, allyl esters of phosphoric acid and phosphorous acid and allyl phosphoramido compounds, such as phosphoric acid monoethyl ester N,N-diallyldiamide, and mixtures of these monomers. Divinyldioxane, di-, tri-, tetra- and pentaallyl sucrose, pentaerythritol triallyl ether and/or N,N'-methylenebisacrylamide are preferably used as crosslinking agents. The crosslinking agent to be used in the copolymerization either alone or as a mixture. The monomer mixtures used in the polymerization contain the monomers of group (b) in an amount of from 0.001 to 10, preferably from 0.05 to 5, % by weight.

To modify the crosslinked copolymers, other ethylenically unsaturated monomers can be used in the copolymerization. The group of monomers (c) includes, for example, acrylonitrile, methacrylonitrile, acrylates and methacrylates derived from monohydric $C_1$–$C_{18}$-alcohols, hydroxy-$C_2$–$C_4$-alkyl esters of acrylic acid and methacrylic acid, maleic anhydride, vinyl esters, 2-acrylamido-2-methylpropylsulfonic acid and/or vinylphosphonic acid. Esters of acrylic acid and methacrylic acid with fatty alcohol oxyethylates and fatty alcohol oxypropylates are also suitable, the fatty alcohol component being of 10 to 20 carbon atoms and the ethylene oxide or prooylene oxide content being of 10 to 20 mol %. Such alcohol components are obtained, for example, by reacting $C_{10}$–$C_{20}$-fatty alcohols with ethylene oxide and/or propylene oxide and esterifying the resulting oxyalkylated fatty alcohols with acrylic acid or methacrylic acid. The use of these comonomers gives crosslinked copolymers which have high electrolyte stability. The monomers of group (c) are used in an amount of from 0 to 20, preferably not more than 15, % by weight. Where they are employed for modifying the copolymers from (a) and (b), the lower limit is 5% by weight, based on the monomer mixture. The sum of the percentages for the monomers (a), (b) and (c) is 100% in every case. Examples of esters of acrylic acid and methacrylic acid are methyl acrylate, ethyl acrylate, methyl methacrylate, 2-ethylhexyl acrylate, stearyl acrylate, stearyl methacrylate and the acrylates of the isomeric butyl alcohols. Examples of suitable hydroxy-$C_2$–$C_4$-alkyl esters of acrylic acid and methacrylic acid are hydroxyethyl acrylate, hydroxypropyl acrylate, hydroxybutyl acrylate, hydroxyethyl methacrylate, hydroxypropyl methacrylate and hydroxybutyl methacrylate. Preferably used vinyl esters are vinyl acetate and vinyl propionate.

The copolymerization is carried out under superatmospheric pressure in supercritical carbon dioxide as an inert diluent. The properties of carbon dioxide in the liquid state and in the supercritical state are reported by J. A. Hyatt in *J. Org. Chem.* 49 (1984), 5097–5101. According to this publication, the critical point of carbon dioxide is about 31° C. and 73 bar. In every case, the copolymerization is carried out under superatmospheric pressure in supercritical carbon dioxide at above about 31° C., the critical temperature of carbon dioxide. The upper limit for the preparation of the copolymers is regarded as the temperature which is 10° below the beginning of the softening range of the particular copolymer formed. The upper value of this temperature limit is 150° C. for most copolymers. The copolymerization is preferably carried out at from 40° to 130° C. The pressures employed during the procedure are above 73 bar, preferably from 80 to 300 bar.

The polymerization reaction is started with the aid of a free radical polymerization initiator. All initiators which are known for the polymerization of the monomers can be used. For example, free radical initiators which have a half life of less than 3 hours at the particular temperatures chosen are suitable. If the polymerization is carried out at two different temperatures by first subjecting the monomers to initial polymerization at a lower temperature and then completing the polymerization at a substantially higher temperature, it is advantageous to use two or more different initiators which have an adequate rate of decomposition in the particular temperature range chosen. For example, the following initiators can be used in the temperature ranges stated below:

Temperature: 40°–60° C.
Acetylcyclohexanesulfonyl peroxide, diacetyl peroxydicarbonate, dicyclohexyl peroxydicarbonate, di-2-ethylhexyl peroxydicarbonate, tert.-butyl perneodecanoate and 2,2'-azobis-(4-methoxy-2,4-dimethylvaleronitrile)

Temperature: 60°–80° C.
tert.-Butylperpivalate, dioctanoyl peroxide, dilauroyl peroxide, 2,2'-azobis-(2,4-dimethylvaleronitrile) and tert.-butylazo-2-cyanobutane Temperature: 80°–100° C.
Dibenzoyl peroxide, tert.-butyl per-2-ethylhexanoate, tert.-butyl permaleate and 2,2-azobis isobutyronitrile Temperature: 100°–120° C.
bis-(tert.-Butylperoxy)-cyclohexane, tert.-butylperoxyisopropyl carbonate and tert.-butyl peracetate Temperature: 120°–140° C.
2,2-Bis-(tert.-butylperoxy)-butane, dicumyl peroxide, di-tert.-amyl peroxide and di-tert.-butyl peroxide Temperature: 140°–160° C.
p-Menthane hydroperoxide, pinane hydroperoxide, cumene hydroperoxide and tert.-butyl hydroperoxide.

By concomitantly using redox coinitiators, for example benzoin, dimethylaniline and heavy metal complexes and salts which are soluble in organic solvents, e.g. copper, cobalt, manganese, iron, nickel and chromium complexes and salts of this type, the half-lives of the stated peroxides, in particular the hydroperoxides, can be reduced so that, for example, tert.-butyl hydroperoxide is effective at as low as 100° C. in the presence of 5 ppm of copper(II) acetylacetonate.

The polymerization initiators are used in the amounts conventionally employed for polymerization; for example, from 0.05 to 10, preferably from 0.1 to 5, parts by weight of an initiator are required per 100 parts by weight of the monomers.

The polymerization can, if required, also be carried out in the presence of a polymerization regulator in order to control the molecular weight of the polymers. If it is intended to prepare particularly low molecular weight copolymers, larger amounts of polymerization regulators are used, whereas high molecular weight copolymers are prepared using only small amounts of polymerization regulators if any at all. Examples of suitable polymerization regulators are 2-mercaptoethanol, mercaptopropanols, mercaptobutanols, thioglycolic acid, N-dodecylmercaptan, tert.-dodecylmercaptan, thiophenol, mercaptopropionic acid, allyl alcohol and acetaldehyde. The polymerization regulators are used in an amount of from 0 to 10, preferably from 0.1 to 5, % by weight, based on the monomers used.

From 100 to 1,500, preferably from 200 to 900, parts by weight of carbon dioxide are used per 100 parts by weight of the monomer mixture, the carbon dioxide preferably being anhydrous. The polymerization reaction can be carried out batchwise or continuously with thorough mixing of the reactants in appropriately designed pressure apparatus. In order to remove the heat evolved during the polymerization, it is desirable for the pressure apparatuses to possess a cooling system. They must of course also be heatable in order to heat the reaction mixture to the particular temperature desired for the polymerization. The pressure apparatuses should have mixing means, for example stirrers (paddle stirrer, impeller stirrers or multistage impulse countercurrent agitators) or blades.

The pressure polymerization can be carried out, for example, as follows. The monomers and the initiator are initially taken in a pressure apparatus, the carbon dioxide is introduced in liquid form, the autoclave is closed and the reaction mixture is then brought to the polymerization temperature. However, it is also possible for only some of the reaction mixture to be initially taken in the autoclave and heated to the polymerization temperature and further reaction mixture to be pumped in at a rate corresponding to the rate of polymerization. In another possible procedure, only some of the monomers in the total amount of carbon dioxide required are initially taken in the autoclave, and the monomers are pumped into the autoclave together with the initiator at the rate at which polymerization proceeds. When the polymerization reaction is complete, the reaction mixture is cooled if necessary and the carbon dioxide is separated off. The copolymers are obtained as a pulverulent residue. The particle size of the powder is from 0.5 $\mu$m to 5 mm, preferably from 1 $\mu$m to 0.5 mm, these particles consisting of primary particles of 0.5-3 $\mu$m diameter and being more or less loosely aggregated. The carbon dioxide separated off can be reliquefied and reused for the polymerization without expensive purification.

The high molecular weight crosslinked copolymers prepared according to the invention can be used, for example, as thickeners for aqueous systems, for example in textile printing pastes, cosmetic and pharmaceutical formulations, emulsion paints, adhesives and oil drilling fluids. The high molecular weight crosslinked copolymers based on acrylic acid and/or methacrylic acid are preferably used in amounts of from 0.1 to 5% by weight in cosmetic and pharmaceutical formulations, such as creams and ointments.

Those crosslinked copolymers which contain free carboxyl groups give, after neutralization with an aqueous base, clear gels which are regarded as free-flowing to stiff, depending on the concentration for use. The thickening action of these copolymers is achieved by neutralization of the carboxyl groups, the optimum thickening effect being obtained at a pH of from 6.0 to 10.0, preferably from 7.0 to 9.0. Neutralization is effected using, in the main, sodium hydroxide, potassium hydroxide, sodium carbonate, potassium carbonate, ammonia or a mixture of these bases, as well as amines, for example tri-$C_1$-$C_5$-alkylamines or mono-, di- or tri-$C_1$-$C_4$-alkanolamines or mixtures of these. Crosslinked copolymers based on amides result in an increase in viscosity in aqueous systems, at both acidic and alkaline pH. In the acidic pH range, crosslinked dialkylaminoalkyl acrylates and methacrylates lead to a sharp increase in the viscosity of the aqueous system. In order to obtain reproducible values when testing the thickening effect of the crosslinked copolymers, the viscosity of the thickened aqueous system was measured as described below.

490 g of fully demineralized water were initially taken in a 600 ml beaker. 5 g of the pulverulent crosslinked copolymer were then sprinkled in while stirring with a blade stirrer at a speed of about 100 rpm, sprinkling being effected in such a way that formation of lumps of the powder in the water was avoided. The mixture was stirred for 10 minutes and left to stand for 10 minutes, 5 g of aqueous 25% strength ammonia were added and the mixture was then homogenized. The pH of the mixture should be from 8 to 9. In order to obtain results which correspond closely to practice, a sample of 250 g of the mixture was stirred for 3 minutes with a high speed stirrer (propellor diameter 3.5 cm) at 8,000 rpm. The temperature of this sample was then brought to 20° C., after which the viscosity was measured in a Haake viscotester VT 24 at 5.66 rpm.

In the Examples which follow, parts and percentages are by weight.

EXAMPLE 1

15 g of acrylic acid, 0.075 g of pentaerythritol triallyl ether and 0.075 g of tert.-butyl perethylhexanoate are initially taken in an autoclave having a capacity of 300 ml. 135 g of liquid carbon dioxide are added and the autoclave, which is equipped with a stirrer and an electric heater, is closed. The reaction mixture is stirred at 300 rpm and heated to 80° C. A maximum pressure of 150 bar is reached. After a residence time of the reaction mixture of 5 hours at 80° C. under 150 bar, the content of the autoclave is cooled and the pressure is let down. The resulting loose white powder is composed of aggregates having a particle size of from 15 to 500 $\mu$m. The size of the primary particles is about 1 $\mu$m. In the above test method for the thickening effect of copolymers, the aqueous solution is found to have a viscosity of 7,000 mPa.s.

EXAMPLES 2 TO 16

Example 1 is repeated with the starting materials stated in the Table below and under the other conditions (temperature, pressure and time). In every case, a loose white pulverulent copolymer having a particle size of from 15 to 500 $\mu$m is obtained. The size of the primary particles in each case is from about 1 to 3 $\mu$m. The copolymers are thickners, and the thickening effect according to the above test method is likewise shown in the Table.

TABLE

| Example | $CO_2$ [g] | Monomer (a) [g] | Monomer (a) O or (c) | Monomer (b) [g] | Monomer (b) | Initiator [g] | Temp. [°C] | Pressure [bar] | Time [h] | Thickening effect (Viscosity) [mPa.s] |
|---|---|---|---|---|---|---|---|---|---|---|
| 2 | 135 | 15 | acrylic acid | 0.06 | pentaerythritol triallyl ether | 0.075 ABDV[(1)] | 70 | 140 | 10 | 2800 |
| 3 | 135 | 15 | acrylic acid | 0.06 | pentaerythritol triallyl ether | 0.038 ABDV | 60 | 135 | 10 | 5400 |
| 4 | 135 | 15 | acrylic acid | 0.075 | pentaerythritol triallyl ether | 0.038 ABDV | 60 | 130 | 10 | 1800 |
| 5 | 135 | 15 | acrylic acid | 0.06 | divinyldioxane | 0.038 ABDV | 70 | 140 | 11 | 5000 |
| 6 | 135 | 15 | acrylic acid | 0.075 | pentaerythritol triallyl ether | 0.15 TBPEH[(2)] | 80 | 160 | 5 | 11600 |
| 7 | 135 | 15 | acrylic acid | 0.075 | pentaerythritol triallyl ether | 0.15 AIBN[(3)] | 80 | 160 | 5 | 4800 |
| 8 | 135 | 12 3 | acrylic acid methacrylic acid | 0.06 | pentaerythritol triallyl ether | 0.038 ABDV | 60 | 120 | 10 | 26400 |
| 9 | 135 | 12 3 | acrylic acid methacrylic acid | 0.075 | pentaerythritol triallyl ether | 0.038 ABDV | 60 | 120 | 10 | 9600 |
| 10 | 135 | 12 3 | acrylic acid methacrylic acid | 0.06 | pentaerythritol triallyl ether | 0.038 ABDV | 60 | 120 | 10 | 16200 |
| 11 | 135 | 15 | methacrylic acid | 0.10 | pentaerythritol triallyl ether | 0.038 ABDV | 60 | 120 | 10 | 1800 |
| 12 | 120 | 30 | acrylic acid | 0.12 | pentaerythritol triallyl ether | 0.3 ABDV | 70–110 | 145–200 | 10 | 3400 |
| 13 | 135 | 13.5 1.5 | Acrylic acid Lauryl acrylate | 0.075 | Pentaerythritol triallyl ether | 0.075 ABDV | 70 | 140 | 10 | 9500 |
| 14 | 135 | 13.5 1.5 | Acrylic acid Maleic anhydride | 0.075 | Pentaerythritol triallyl ether | 0.075 ABDV | 70 | 140 | 10 | 2300 |
| 15 | 135 | 9 3 3 | Acrylic acid Methacrylic acid Acrylamide | 0.06 | Pentaerythritol triallyl ether | 0.038 ABDV | 60 | 120 | 10 | 8600 |
| 16 | 135 | 11.5 1.5 1.5 1.5 | Acrylic acid Dimethylaminoethyl acrylate Methacrylamide Acrylamidomethylpropylsulfonic acid | 0.06 | Pentaerythritol triallyl ether | 0.038 ABDV | 60 | 120 | 10 | 2300 |

[(1)]ABDV = 2,2'-azobis-(2,4-dimethylvaleronitrile)
[(2)]TBPEH = tert.-butyl perethylhexanoate
[(3)]AIBN = 2,2'-azobisisobutyronitrile

We claim:

1. A process for the preparation of a pulverulent crosslinked copolymer, comprising polymerizing a monomer mixture consisting of
   (a) from 70 to 99.999% by weight of monoethylenically unsaturated carboxylic acids, amides of such carboxylic acids and/or esters of such carboxylic acids and amino alcohols of the formula

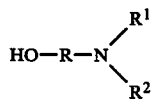

where R is $C_2$–$C_6$-alkylene and $R^1$ and $R^2$ are each H, $CH_3$, $C_2H_5$ or $C_3H_7$,
   (b) from 0.001 to 10% by weight of a diethylenically or polyethylenically unsaturated monomer and
   (c) from 0 to 20% by weight of other monoethylenically unsaturated monomers in supercritical carbon dioxide at up to 150° C. and under pressures above 73 bar in the presence of a free radical initiator, from 100 to 1,500 parts by weight of carbon dioxide being used per 100 parts by weight of the monomers employed in the polymerization, and removing the carbon dioxide after the polymerization resulting in a fine polymer powder consisting of primary particles of 0.5 μm to 3 μm in diameter.

2. A process as claimed in claim 1, wherein from 200 to 900 parts by weight of carbon dioxide are used per 100 parts by weight of the monomers.

3. A process as claimed in claim 1, wherein
   (a) monoethylenically unsaturated $C_3$–$C_5$-carboxylic acids, amides of ethylenically unsaturated $C_3$–$C_5$-carboxylic acids and/or di-$C_1$–$C_3$-alkylamino-$C_2$–$C_6$-alkyl acrylates or methacrylates in the form of the salts or in quaternizied form,
   (b) divinyldioxane, polyalkyl and polyvinyl ethers of mono-, di- and oligosaccharides, N,N'-methylenebisacrylamide, N,N'-methylenebismethacrylamide, di- and triallyl ethers of trimethylolpropane and glycerol, and pentaerythritol triallyl ether, and
   (c) acrylonitrile, methacrylonitrile, acrylates and methacrylates of monohydric $C_1$–$C_{18}$-alcohols, hydroxy-$C_2$–$C_4$-alkyl esters of acrylic acid and methacrylic acid, maleic anhydride, vinyl esters and/or vinylphosphonic acid are used as the monomer mixture.

4. A process as claimed in claim 1, wherein
   (a) from 70 to 99.95% by weight of acrylic acid, methacrylic acid, acrylamide and/or methacrylamide,
   (b) from 0.05 to 5% by weight of divinyldioxane, di-, tri-, tetra- and pentaallyl sucrose or mixtures of these, pentaerythritol triallyl ether or N,N'-methylenebisacrylamide and/or (c) from 0 to 20% by weight of acrylates and methacrylates of monohydric $C_1$–$C_{18}$-alcohols, hydroxy-$C_2$–$C_4$-alkyl esters of acrylic acid and methacrylic acid, maleic anhydride, vinyl acetate, vinyl propionate and/or vinylphosphonic acid are used as the monomer mixture.

5. A process as claimed in claim 1, wherein
(a) acrylic acid or methacrylic acid and
(b) pentaerythritol triallyl ether or N,N'-methylenebisacrylamide are used as the monomer mixture.

6. A process as claimed in claim 1, wherein tert.butyl per-2-ethylhexanoate, 2,2'-azobis-(2,4-dimethylvaleronitrile), 2,2'-asobis-(4-methoxy-2,4-dimethylvaleronitrile), 2,2'-azobis-isobutyronitrile or 2,2'-azobis-(2-amidinopropane) dihydrochloride is used as the free radical initiator.

* * * * *

UNITED STATES PATENT AND TRADEMARK OFFICE
CERTIFICATE OF CORRECTION

PATENT NO. : 4,748,220

DATED : May 31, 1988

INVENTOR(S) : HEINRICH HARTMANN and WALTER DENZINGER

It is certified that error appears in the above-identified patent and that said Letters Patent is hereby corrected as shown below:   On The Title Page:

First page, Bibliographic Data, add Code 30 - Foreign Application Priority Data - March 22, 1986 (DE) Fed. Rep. of Germany - 3609829.

Signed and Sealed this

Eighteenth Day of October, 1988

Attest:

DONALD J. QUIGG

*Attesting Officer*          *Commissioner of Patents and Trademarks*